United States Patent
Stolz et al.

(10) Patent No.: US 11,926,585 B2
(45) Date of Patent: Mar. 12, 2024

(54) PROCESS FOR THE PRODUCTION OF ALUMINUM SALTS OF A FATTY ACID

(71) Applicant: Peter Greven GmbH & Co. KG, Bad Münstereifel (DE)

(72) Inventors: Hermann Josef Stolz, Bad Münstereifel (DE); Wilhelm Huber, Kerpen (DE); Gabriel Kehren, Euskirchen (DE)

(73) Assignee: Peter Greven GmbH & Co., KG, Bad Münstereifel (DE)

( * ) Notice: Subject to any disclaimer, the term of this patent is extended or adjusted under 35 U.S.C. 154(b) by 0 days.

(21) Appl. No.: 17/674,252

(22) Filed: Feb. 17, 2022

(65) Prior Publication Data

US 2022/0267243 A1   Aug. 25, 2022

(30) Foreign Application Priority Data

Feb. 19, 2021   (EP) .................................. 21158204

(51) Int. Cl.
   *C07C 51/41*   (2006.01)
(52) U.S. Cl.
   CPC ................. *C07C 51/412* (2013.01)
(58) Field of Classification Search
   CPC ..... C07C 51/01; C07C 51/412; C07C 53/126; C07C 51/41
   See application file for complete search history.

(56) References Cited

U.S. PATENT DOCUMENTS

| | | | |
|---|---|---|---|
| 2,417,071 A * | 3/1947 | Gebhart | C07C 51/412 |
| | | | 556/133 |
| 2,447,064 A * | 8/1948 | Gebhart | C07C 51/412 |
| | | | 106/13 |
| 2,469,041 A * | 5/1949 | Jones | C10M 5/00 |
| | | | 106/14.13 |
| 3,056,819 A * | 10/1962 | Tanabe | C07C 51/412 |
| | | | 554/76 |

FOREIGN PATENT DOCUMENTS

GB           338919 A *   2/1930   ........... C07C 51/412

OTHER PUBLICATIONS

Loncar, E.S., et al., Preparation and characterization of aluminum stearate, Acta Periodical Technologica APTEFF, 34, 1-148, pp. 55-60 (Year: 2003).*
Glazer, J., et al., The preparation of a stable aluminum dodecanoate (laurate) with No. gelling properties in hydrocarbons, Department of Colloid Science, The University of Cambridge, 2 pages (Year: 1950).*
Loncar et al., "Preparation and Characterization of Aluminum Stearate", Acta Periodica Technologica APTEFF, p. 55-60, (Jan. 1, 2003).
Search Reporting from corresponding European Patent Application No. 21158204.4 dated Aug. 26, 2021.

* cited by examiner

*Primary Examiner* — Yate' K Cutliff
(74) *Attorney, Agent, or Firm* — Christensen, Fonder, Dardi PLLC; Diane E. Bennett; Peter S. Dardi

(57) ABSTRACT

A process for the production of aluminum salts of a fatty acid, comprising the following steps:
  a) mixing a fatty acid and an aqueous solution of a strong base to prepare an aqueous base/fatty acid mixture,
  b) mixing said aqueous base/fatty acid mixture with an aluminum source to prepare an aqueous base/fatty acid/aluminum mixture,
  c) mixing said aqueous base/fatty acid/aluminum mixture with an acid, and
  d) separating the produced aluminum salts of the fatty acid.

16 Claims, No Drawings

PROCESS FOR THE PRODUCTION OF ALUMINUM SALTS OF A FATTY ACID

This application claims priority to EP patent application 21158204.4 to Stolz et al., entitled "Verfahren zur Herstellung von Aluminiumsalzen einer Fettsäure," incorporated herein by reference.

The present invention relates to a process for the production of aluminum salts of a fatty acid, and to aluminum salts of a fatty acid obtainable by such a process.

Aluminum salts of fatty acids are also referred to as aluminum soaps. They have hydrophobic properties and are characterized by a waxy consistency. Because of the trivalency of the aluminum ions contained, aluminum salts of fatty acids can be in the form of mono-, di- or trifatty acid aluminum salts. The mono- or difatty acid aluminum salts may contain hydroxide ions as additional counter ions for the trivalent aluminum ion, in addition to the fatty acid anions. The hydroxide ions contained in the mono- or difatty acid aluminum salts provide the aluminum salts of the fatty acid with dispersing properties. Thus, the aluminum salts of fatty acids are suitable for thickening oils, and may be used in the pharmaceutical industry or cosmetics industry, for example, for the production of creme or ointment bases.

The industrial production of aluminum salts from fatty acids is effected predominantly by the precipitation method ("double reaction"). At first, in a first reaction step, a sodium salt of a fatty acid is formed in an aqueous solution. In a second reaction step, the aluminum salt of the fatty acid is precipitated by adding aluminum sulfate or chloride. A disadvantage of this method is the fact that the salts sodium sulfate or chloride, which are formed as by-products, cannot be separated from the aluminum salt of the fatty acid easily. Washing out the by-products completely or almost completely can be realized only with a great effort.

This is a disadvantage, in particular, with respect to an application of the aluminum salts of fatty acids in the pharmaceutical industry. Aluminum salts of fatty acids, for example, aluminum stearates, are used in the pharmaceutical industry, for example, for the production of capsules, inhalation sprays, or ointments. According to the European Pharmacopoeia (*Pharmacopoea Europaea*, Ph. Eur.), for example, the content of chloride in aluminum stearate is limited to 1000 ppm, the content of sulfate is limited to 5000 ppm. Since the by-products sodium sulfate and sodium chloride formed in the above described precipitation method can be removed from the product only with a great effort, the required low chloride and sulfate contents cannot be realized in an economically efficient way.

Loncar et al., APTEFF34 (2003) 1-148, describes the production and characterization of aluminum stearates.

U.S. Pat. No. 2,469,041 describes another process for the production of aluminum salts of fatty acids. In this process, the aluminum alcoholates of lower molecular weight alcohols are prepared at first. They are directly reacted with the desired fatty acids in an oil matrix. The by-products of the reaction, i.e., lower molecular weight alcohols, are evaporated. However, it is disadvantageous that the method described is suitable only for the in-situ preparation of greases.

Therefore, it has been the object of the present invention to provide a process for the production of aluminum salts of a fatty acid, which overcomes at least part of the problems known from the prior art.

The object of the invention is achieved by a process for the production of aluminum salts of a fatty acid, comprising the following steps:

a) mixing a fatty acid and an aqueous solution of a strong base to prepare an aqueous base/fatty acid mixture,
b) mixing said aqueous base/fatty acid mixture with an aluminum source to prepare an aqueous base/fatty acid/aluminum mixture,
c) mixing said aqueous base/fatty acid/aluminum mixture with an acid, and
d) separating the produced aluminum salts of the fatty acid.

In step a) of the process according to the invention for the production of aluminum salts of a fatty acid, an aqueous base/fatty acid mixture is prepared, by mixing a strong base with water. An aqueous solution of a strong base is thereby obtained. Subsequently, a fatty acid is added to the previously formed aqueous solution of the strong base. The fatty acid is dissolved in the aqueous base solution. Preferably, said aqueous base/fatty acid mixture from step a) comprises a deprotonated fatty acid.

In step b) of the process according to the invention for the production of aluminum salts of a fatty acid, an aqueous base/fatty acid/aluminum mixture is prepared, by adding and mixing an aluminum source with the aqueous base/fatty acid mixture from step a). Preferably, said aluminum source is dissolved in said aqueous base/fatty acid mixture from step a). Preferably, said aluminum source from step b) is an aqueous solution of the aluminum source.

In step c) of the process according to the invention for the production of aluminum salts of a fatty acid, said aqueous base/fatty acid/aluminum mixture from step b) is admixed with an acid. The acid is mixed with said aqueous base/fatty acid/aluminum mixture.

In step d) of the process according to the invention for the production of aluminum salts of a fatty acid, the produced aluminum salts of the fatty acid are separated from the remaining components of the acidified aqueous base/fatty acid/aluminum mixture from step c). The separation of the aluminum salts of the fatty acid from the remaining components of the acidified aqueous base/fatty acid/aluminum mixture may be effected by a physical separation method, such as filtration or centrifugation. Preferably, the separation is effected by filtration. In this case, the aluminum salts of the fatty acid form the filter cake. In order to improve the separation of the produced aluminum salts of the fatty acid from the remaining components, the filter cake may be washed with water, preferably with distilled water. When the separation is effected by centrifugation, the aluminum salts of the fatty acid form the pellet.

The aluminum salts of a fatty acid produced by the process according to the invention may be mono-, di- or trifatty acid aluminum salts.

The fatty acids used in the process according to the invention for the production of aluminum salts of a fatty acid are preferably derived from natural sources. For example, the fatty acids may be obtained from palm oil or palm kernel oil, coconut oil, tallow, castor oil, but also rapeseed or soybean. The fatty acids may be saturated or unsaturated fatty acids.

Preferably, the fatty acids used in the process according to the invention are fatty acids having chain lengths of C6 to C28, or mixtures thereof. More preferably, the fatty acid is selected from the group consisting of stearic acid, palmitic acid, and mixtures of such fatty acids.

In one embodiment of the process according to the invention, the fatty acid is stearic acid. Commercially available stearic acid is predominantly obtained from tallow or palm oil. In accordance with its origin, the commercially available stearic acid usually does not consist of pure stearic (octadecanoic) acid, but has a fatty acid distribution that is typical of its origin. Thus, to be strictly accurate, commercially available stearic acid is often a fatty acid mixture that includes stearic acid. If the stearic acid is obtained from tallow, it contains about 65% by weight of octadecanoic acid and 25% by weight of palmitic (hexadecanoic) acid. If the stearic acid is obtained from palm oil or palm kernel oil, it may have a content of from 50% by weight or 65% by weight of octadecanoic acid. Commercially available stearic acid may also contain significantly less than 50% by weight of octadecanoic acid. The content of hexadecanoic acid is correspondingly higher.

In one embodiment of the process according to the invention, stearic acid obtained from tallow having a content of octadecanoic acid of from 50 to 70% by weight is used as the fatty acid. In another embodiment, stearic acid obtained from palm oil having a content of octadecanoic acid of from 40 to 70% by weight is used.

In another embodiment, stearic acid having a purity of >80% by weight is used. Stearic acid having a purity of ≥98% by weight may also be used.

Preferably, the strong base from step a) is an alkali hydroxide. More preferably, it is sodium hydroxide or potassium hydroxide. More preferably, the strong base is sodium hydroxide. The concentration of the strong base in the aqueous solution of the strong base obtained by mixing the strong base with water is preferably at 0.2 mol/l or more. The concentration is preferably at 1.0 mol/l or less. More preferably, the concentration is from 0.3 mol/l to 0.8 mol/l, more preferably from 0.35 mol/l to 0.75 mol/l.

The pH value of the aqueous base/fatty acid mixture from step a) is preferably within a range of from 7.0 to 12.0, more preferably from 8.0 to 11.0.

Preferably, the aluminum source used in step b) is an alkali aluminate, or aluminum powder. More preferably, the aluminum source is sodium aluminate, or aluminum powder. Even more preferably, the aluminum source is sodium aluminate. Alkali aluminates are salts of aluminic acid $HAlO_2 \times H_2O$, in which aluminum forms a complex anion $[Al(OH)_4]^-$ with a hydroxide ion as a ligand, and salts in which the anion is present as a condensate of the aluminate ion. The general composition of such compounds is $M[Al(OH)_4]$, wherein M is an alkali cation, preferably $Na^+$. Completely condensed anhydrous compounds have the general composition $MAlO_2$ with $AlO_2^-$ as the anion, wherein M is an alkali cation, preferably $Na^+$. In step b) of the process according to the invention, commercially available $NaAlO_2$ can be employed as the aluminum source.

Preferably, the concentration of the aluminum source in the aqueous base/fatty acid/aluminum mixture in step b) is from 50 mmol/l to 600 mmol/l, more preferably from 100 mmol/l to 500 mmol/l, respectively measured as aluminum. Methods for the quantitative determination of aluminum are known to those skilled in the art. For example, the content of aluminum may be determined by means of atomic absorption spectrometry (AAS). In this method, the total quantity of aluminum (total aluminum) is determined.

Preferably, the acid used in step c) of the process according to the invention is an organic acid, an inorganic acid, or a mixture thereof. Said organic acid is preferably a monocarboxylic acid, more preferably formic acid or acetic acid, even more preferably acetic acid. Preferably, said inorganic acid is selected from the group consisting of phosphoric acid, hydrochloric acid, nitric acid, sulfuric acid, or any of their derivatives. In a preferred embodiment, said inorganic acid is phosphoric acid. In step c), hydrochloric acid or sulfuric acid may be used. In such a case, amounts of the acid are used that result in the content of chloride in the product being at most 1000 ppm, and/or the content of sulfate in the product being at most 5000 ppm.

In a preferred embodiment of the process according to the invention, the acid used in step c) is an organic acid, preferably a monocarboxylic acid, more preferably formic acid or acetic acid, even more preferably acetic acid.

After the mixing of the aqueous base/fatty acid/aluminum mixture with the acid in step c), the pH value of the acidified aqueous base/fatty acid/aluminum mixture is within a range of from 3.5 to 7.0. Preferably, the pH value is from 4.5 to 7.0. More preferably, the pH value is from 5.0 to 6.0, or from 5.3 to 5.8.

In one embodiment of the process according to the invention, the fatty acid and the aqueous solution of a strong base from step a) are mixed with an aromatic carboxylic acid, preferably benzoic acid, and/or derivatives of benzoic acid. Preferably, said mixing with the aromatic carboxylic acid is effected before the aluminum source is added to the aqueous base/fatty acid mixture. More preferably, the aromatic carboxylic acid is mixed with the aqueous solution of said strong base, before the fatty acid is added. The aluminum salts of a fatty acid formed in this embodiment are so-called aluminum complex soaps. In addition to the fatty acid anions, they also contain anions of the aromatic carboxylic acid. The aluminum complex soaps are suitable, in particular, for the production of grease.

Surprisingly, it has been found that aluminum salts of a fatty acid produced by the process according to the invention have a low content of sodium chloride and sodium sulfate and other salts. If acetic acid is used as the acid in step c) of the process according to the invention, an alkali acetate is formed as a by-product of the aluminum salts of the fatty acid, and can be washed out easily. For example, aluminum stearate produced by the process according to the invention has a chloride content of at most 1000 ppm, and a sulfate content of at most 5000 ppm, and thus meets the requirements of the European Pharmacopoeia. In addition, the surprisingly low total sodium content of the aluminum salts of the fatty acids obtained by the process according to the invention proves advantageous.

The invention further relates to aluminum salts of a fatty acid, which are obtainable by the process according to the invention for the production of aluminum salts of a fatty acid. Preferably, said aluminum salts of a fatty acid have a chloride content of at most 1000 ppm, and/or a sulfate content of at most 5000 ppm. The chloride content is determined according to the protocol of the European Pharmacopoeia mentioned in the monograph relating to aluminum stearate (European Pharmacopoeia, Edition 10.0 (2019): "Monographs A", 'Aluminium Stearate' und "Methods of Analysis", '2.4.4 Chlorides'). The sulfate content is determined according to the protocol of the European Pharmacopoeia mentioned in the monograph relating to aluminum stearate (European Pharmacopoeia, Edition 10.0 (2019): "Monographs A", 'Aluminium Stearate' und "Methods of Analysis", '2.4.13 Sulfates').

Unless stated otherwise, all volumes are measured at 23° C. Unless stated otherwise, the designation "ppm" represents the mass proportion. Consequently, a chloride content of the aluminum salts of a fatty acid of at most 1000 ppm means that 1 kg of product contains at most 1000 mg of chloride.

The invention is further illustrated by means of the following Examples.

The sodium content of the products obtained in Examples 1 to 5 was determined by means of X-ray fluorescence analysis. In this method, the total quantity of sodium (total sodium) was determined.

EXAMPLE V: EXPERIMENTS FOR THE PREPARATION OF LOW CHLORIDE AND LOW SULFATE ALUMINUM FATTY ACID SALTS (COMPARATIVE EXAMPLES)

Aluminum stearate was obtained on an industrial scale by reacting stearic acid with aqueous sodium hydroxide solution, and precipitation with aluminum sulfate. It is a white solid that is insoluble and floating in water. After filtering off, the product has a high water content.

The sulfur content was measured by X-ray fluorescence analysis. Because the molecular weight of sulfur is 32 g/mol and that of sulfate is 96 g/mol, the sulfate content is three times as high as the sulfur content. In addition, the water content of aluminum stearate must be taken into account. It is on the order of 70% by weight and was measured for each sample.

| Sample | Treatment | Sulfate content (calculated) [ppm] |
|---|---|---|
| Starting material | | 19000 |
| Mix 1 | 3 washes for 900 s with 60 weight parts of town water, 60° C., 10 s pressing of the filter | 17700 |
| Mix 2 | 1 wash for 900 s with 60 weight parts of town water, 60° C., 10 s pressing of the filter | 17700 |
| Mix 3 | 1 wash for 900 s with 60 weight parts of town water, 20° C., 10 s pressing of the filter | 19100 |
| Mix 4 | 1 wash for 900 s with 60 weight parts of demineralized water, 20° C., 10 s pressing of the filter | 15500 |
| Mix 5 | 1 wash for 600 s with 100 weight parts of town water, 20° C., 10 s pressing of the filter | 17100 |
| Mix 6 | 1 wash for 600 s with 100 weight parts of town water, 20° C., without pressing of the filter | 18300 |
| Mix 7 | 1 wash for 600 s with 100 weight parts of town water, 20° C., without pressing of the filter | 18300 |
| Mix 8 | 1 wash for 600 s with 100 weight parts of town water, 20° C., 10 s pressing of the filter | 19100 |
| Mix 9 | 1 wash for 1200 s with 100 weight parts of town water, 20° C., 10 s pressing of the filter | 19300 |

A sufficient reduction of the sulfate content could not be achieved by washing under different conditions.

Example 1: Synthesis of an Aluminum Mono-Di-Stearate

In a beaker, 1.5 l of distilled water was charged, and heated at 80° C. Subsequently, 43 g of solid sodium hydroxide was dissolved in the water. It is slowly saponified by adding 270 g of liquid vegetable-based stearic acid (70° C.). The stearic acid has a content of 66% by weight stearic acid and 27% by weight palmitic acid. Subsequently, 64.5 g of sodium aluminate, which had previously been dissolved in 250 g of water, was slowly added. After a stirring time of 15 minutes, the solution is acidified to a pH value of about 5.5 using 210 g of 60% acetic acid. After another 10 minutes of stirring time, the product is filtered off through a suction filter, and washed several times with distilled water. Drying is effected in a drying cabinet at 80° C. to a water content of <1.5%. The product shows the following analytical data:
Aluminum content: 5.6% by weight
Free fatty acid: 1.6% by weight
Sodium content: <10 ppm
Water content: 0.7% by weight.

Example 2: Synthesis of an Aluminum Di-Tri-Stearate

In a beaker, 2 l of distilled water was charged, and heated at 70-80° C. Subsequently, 31.6 g of solid sodium hydroxide was dissolved in the water. It is slowly saponified by adding 185 g of liquid tallow-based stearic acid (70° C.). Subsequently, 24.6 g of sodium aluminate, which had previously been dissolved in 180 g of water, was slowly added. After a stirring time of 15 minutes, the solution is acidified to a pH value of about 5.5 using 84 g of 60% acetic acid. After another 10 minutes of stirring time, the product is filtered off through a suction filter, and washed several times with distilled water. Drying is effected in a drying cabinet at 80° C. to a water content of <1.5%. The product shows the following analytical data:
Aluminum content: 3.9% by weight
Free fatty acid: 12.2% by weight
Sodium content: <10 ppm
Water content: 1.1% by weight.

Example 3: Synthesis of an Aluminum Tri-Stearate

In a beaker, 1.5 l of distilled water was charged, and heated at 70-80° C. Subsequently, 29.2 g of solid sodium hydroxide was dissolved in the water. It is slowly saponified by adding 194 g of liquid vegetable-based stearic acid (70° C.). The stearic acid has a content of 55% by weight stearic acid and 45% by weight palmitic acid. Subsequently, 21.2 g of sodium aluminate, which had previously been dissolved in 250 g of water, was slowly added. After a stirring time of 15 minutes, the solution is acidified to a pH value of about 5.5 using 73 g of 60% acetic acid. After another 10 minutes of stirring time, the product is filtered off through a suction filter, and washed several times with distilled water. Drying is effected in a drying cabinet at 80° C. to a water content of <1.5%. The product shows the following analytical data:
Aluminum content: 3.4% by weight
Free fatty acid: 18.3% by weight
Sodium content: <10 ppm
Water content: 0.8% by weight.

Example 4: Synthesis of an Aluminum Mono-Di-Stearate

In a beaker, 1.5 l of distilled water was charged, and heated at 80° C. Subsequently, 43 g of solid sodium hydroxide was dissolved in the water. It is slowly saponified by adding 270 g of liquid vegetable-based stearic acid (70° C.). The stearic acid has a content of 66% by weight stearic acid and 27% by weight palmitic acid. Subsequently, 64.5 g of sodium aluminate, which had previously been dissolved in 250 g of water, was slowly added. After a stirring time of 15 minutes, the solution is acidified to a pH value of about 5.5 using 82.3 g of 85% phosphoric acid. After another 10 minutes of stirring time, the product is filtered off through a suction filter, and washed several times with distilled water.

Drying is effected in a drying cabinet at 80° C. to a water content of <1.5%. The product shows the following analytical data:
Aluminum content: 5.2% by weight
Free fatty acid: 2.2% by weight
Sodium content: <10 ppm
Water content: 1.2% by weight.

Example 5: Synthesis of an Aluminum Complex Soap

In a beaker, 1.5 l of distilled water was charged, and heated at 80° C. Subsequently, 43 g of solid sodium hydroxide was dissolved in the water. It is slowly saponified by adding 26.8 g of solid benzoic acid. This is followed by adding 210 g of liquid vegetable-based stearic acid. Subsequently, 64.5 g of sodium aluminate, which had previously been dissolved in 250 g of water, was slowly added. After a stirring time of 15 minutes, the solution is acidified to a pH value of about 5.5 using 210 g of 60% acetic acid. After another 10 minutes of stirring time, the product is filtered off through a suction filter, and washed several times with distilled water. Drying is effected in a drying cabinet at 80° C. to a water content of <1.5%. The product shows the following analytical data:
Aluminum content: 5.3% by weight
Free fatty acid: 3.2% by weight
Sodium content: <10 ppm
Water content: 1.2% by weight.

The invention claimed is:

1. A process for the production of aluminum salts of a fatty acid, comprising the following steps:
   a) mixing a fatty acid and an aqueous solution of a strong base to prepare an aqueous base/fatty acid mixture,
   b) mixing said aqueous base/fatty acid mixture with an aluminum source to prepare an aqueous base/fatty acid/aluminum mixture, wherein said aluminum source is an alkali aluminate or aluminum powder,
   c) mixing said aqueous base/fatty acid/aluminum mixture with an acid, and
   d) separating the produced aluminum salts of the fatty acid.

2. The process according to claim 1, wherein said aluminum salts of a fatty acid are mono-, di- or trifatty acid aluminum salts.

3. The process according to claim 1, wherein said fatty acid is a fatty acid having chain lengths of C6 to C28, or mixtures thereof.

4. The process according to claim 1, wherein said fatty acid comprises stearic acid.

5. The process according to claim 1, wherein said strong base is an alkali hydroxide.

6. The process according to claim 1, wherein said aluminum source is sodium aluminate or aluminum powder.

7. The process according to claim 1, wherein the acid used in step c) is an organic acid, an inorganic acid, or a mixture of both.

8. The process according to claim 7, wherein said organic acid is a monocarboxylic acid.

9. The process according to claim 7, wherein said inorganic acid is phosphoric acid, hydrochloric acid, nitric acid, sulfuric acid, or a mixture thereof.

10. The process according to claim 1, wherein the separating of the produced aluminum salts of the fatty acid is effected by a physical separation method.

11. The process according to claim 1, wherein the fatty acid and the aqueous solution of a strong base are mixed with an aromatic carboxylic acid.

12. The process according to claim 1, wherein the pH value of said aqueous base/fatty acid mixture is within a range of from 7 to 12.

13. The process according to claim 1, wherein the pH value of said acidified aqueous base/fatty acid/aluminum mixture is within a range of from 3.5 to 7.

14. The process according to claim 1, wherein said fatty acid is stearic acid, palmitic acid, or a mixture thereof.

15. The process according to claim 1, wherein said strong base is sodium hydroxide or potassium hydroxide.

16. The process according to claim 11, wherein said aromatic carboxylic acid is mixed with the aqueous solution of a strong base before the fatty acid is added.

* * * * *